United States Patent [19]
Dial et al.

[11] Patent Number: 4,805,639
[45] Date of Patent: Feb. 21, 1989

[54] MEDICAL CAP WITH FACE SHIELD

[75] Inventors: Darrell D. Dial; John M. Geesbreght, both of Fort Worth, Tex.

[73] Assignee: CareSystems, Inc., Aledo, Tex.

[21] Appl. No.: 117,974

[22] Filed: Nov. 9, 1987

[51] Int. Cl.$^4$ .................... A62B 9/06; A41D 13/00; A42B 1/06

[52] U.S. Cl. ........................................ 128/857; 2/9; 2/410

[58] Field of Search ................ 2/9, 174, 250, 410; 128/132 R, 132 D, 203.29, 206.19

[56] References Cited

U.S. PATENT DOCUMENTS

| | | | |
|---|---|---|---|
| 2,249,734 | 7/1941 | Tate et al. | 2/174 |
| 2,353,025 | 7/1944 | Gautreaux | 2/174 |
| 2,355,283 | 8/1944 | Diss | 2/174 |
| 2,579,942 | 12/1951 | MacLean | 2/410 |
| 3,241,155 | 3/1966 | Phillips | 2/9 |
| 3,943,575 | 3/1976 | Bolker | 2/205 |
| 4,589,408 | 5/1986 | Singer | 128/132 R |
| 4,593,417 | 6/1986 | Brown, Jr. et al. | 2/209.1 |
| 4,683,596 | 8/1987 | Cole | 2/174 |

Primary Examiner—Robert A. Hafer
Assistant Examiner—Michael Brown
Attorney, Agent, or Firm—James E. Bradley

[57] ABSTRACT

A cap for use by medical attendants provides shielding of the attendant's face for emergency use. The cap is bag-like in shape and is of a gauze-like material. It fits loosely over the user's head, but is retained by elastic around the opening. A transparent plastic shield is located in the central section of the cap. When the cap is worn conventionally, the shield faces upward and is located on top of the user's head. Pulling the forward edge of the cap downward locates the shield in front of the user's face. This shields the user from contact with any body fluids of a trauma victim while the attendant performs emergency treatment.

7 Claims, 1 Drawing Sheet

U.S. Patent    Feb. 21, 1989    4,805,639
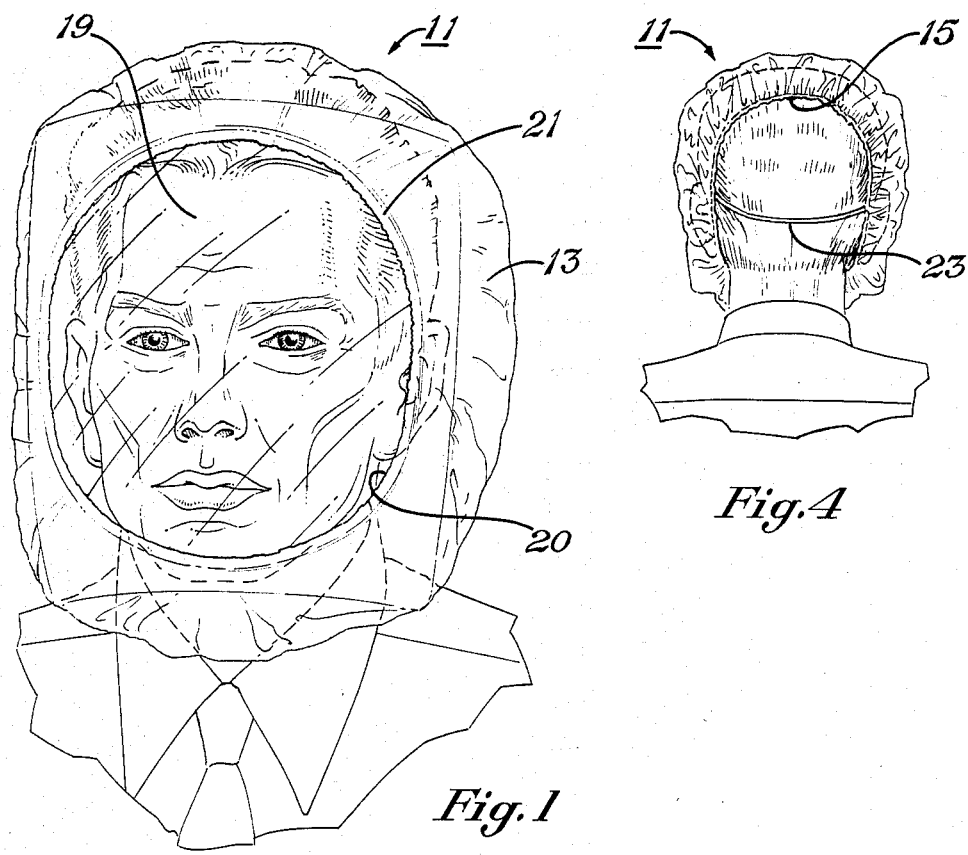
Fig.1
Fig.4
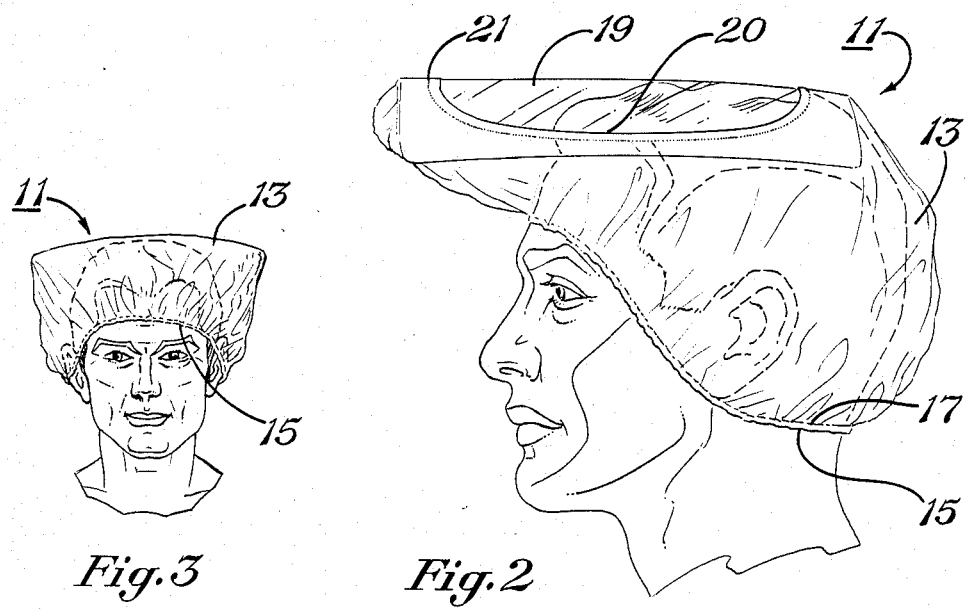
Fig.3    Fig.2

MEDICAL CAP WITH FACE SHIELD

BACKGROUND OF THE INVENTION

1. Field of the Invention

This invention relates in general to protective coverings for medical personnel, and in particular to a device for shielding a medical attendant's face from contact with any body fluids of a patient.

2. Description of the Prior Art

Medical attendants that provide early treatment for trauma victims frequently come into contact with a patient's body fluids. For example, medical personnel for emergency room, ambulance, police and fire departments often must provide fast emergency treatment to patients that are bleeding. It is not uncommon for blood to come into contact with the face of the medical attendant. The body fluids of a trauma victim can transmit communicable infectious diseases to a medical attendant. Infection can occur through chapped lips, abrasions or other means.

In the prior art, there has been no protection for persons providing emergency medical attention. Face masks are not normally worn. Even if worn, a face mask is permeable to liquid and doesn't cover the entire face. Caps are worn by emergency room personnel. These caps do not provide protection against the face being contacted with a patient's body fluids. These caps are worn to prevent hair from the technician from falling into restricted areas.

U.S. Pat. No. 3,943,575 et, Mar. 16, 1976, James H. Bolker, shows a hood which has a plastic face plate. This hood is to be worn by operating room personnel. While this device may be suitable for operating room personnel, it is not practical for emergency room personnel, or other people providing emergency treatment. Such a hood would be cumbersome to be worn continuously by such medical personnel. If not worn continuously, the risk of contact with a patient's body fluids on the face would still exist. It would be unlikely that such emergency personnel in all cases would remember to retrieve such a hood and place it on before coming close to a patient needing emergency treatment.

SUMMARY OF THE INVENTION

A device is provided that will shield the face of the medical attendant from contact with body fluids of a patient requiring emergency treatment. This device is a cap which is similar in overall configuration to caps presently worn by hospital personnel. The cap is bag-shaped, and fits over the user's head above the ears and eyebrows. The cap has elastic that retains it over the user's head. In the normal position worn conventionally on top of the head, the cap serves to prevent hair from falling from the user's head into a restricted area.

The cap has a transparent window or shield formed in the central section. When the cap is worn conventionally, the shield will be on top of the user's head facing upward. If quick emergency treatment is needed, the attendant simply pulls down on the cap to draw the shield in front of his eyes. In the second position, the shield provides visibility for the medical attendant.

BRIEF DESCRIPTION OF THE DRAWINGS

FIG. 1 is a front view of a device constructed in accordance with this invention, and worn in the shielding position.

FIG. 2 is a side view of the cap of FIG. 1, shown being worn in a conventional position.

FIG. 3 is a front view of the cap of FIG. 1, shown being worn in the conventional position.

FIG. 4 is a back view of the cap of FIG. 1, shown being worn in a shielding position.

DESCRIPTION OF THE PREFERRED EMBODIMENT

Referring to FIG. 2, cap 11 is similar in overall size to the caps that are worn by persons in hospitals to prevent hair from the medical person from falling into a restricted area. Cap 11 is in the shape of a flexible bag. It has a top 13 which covers the top of the user's head. It has a single opening 15 into which the user inserts his head. The top 13 is loose so as to fit comfortably over the user, regardless of the amount of hair. Elastic 17 extends around the opening. The elastic causes a rather tight fit about the user's head.

The material of the cap 11 is gauze-like, so that a user can breathe thorugh it. Preferably, it is a spun fibrous material. While not completely impervious to liquid, it does not easily absorb liquid nor allow liquid to pass. The material is translucent.

A transparent shield 19 is secured stationarily in generally the central section of the top 13. Shield 19 is a plastic film, preferably of Mylar. It is also flexible. However, it is stiffer and thicker than the material of the top 13. It preferably is about ten to twenty millimeters in thickness.

The material or sheet forming the shield 19 is rectangular. It is sewn into top 13 within a circular opening 20 that is cut into the top 13. The opening 20 is fairly large, sufficient to cover substantially the entire face of the medical attendant. A seam 21 is formed around the opening 20, securing the shield 19 to the top 13.

An optional strap 23 may be attached across the opening 15, as shown in FIG. 4. Strap 23 is elastic, and is used only when the cap 11 is worn in the shielding position. It fits across the back of the attendant's head to provide extra retension for the cap 11 while in the shielding position. Strap 23 is particularly useful for medical personnel who provide medical treatment out-of-doors, for avoiding the cap 11 from being blown off during windy days.

In operation, the medical attendant normally wears the cap 11 in a position shown in FIG. 2. Particularly with emergency room personnel, such a cap is to be worn at all times. In this position, the shield 19 is directly on top of the attendant's head. It faces upward. The elastic 17 secures the cap 11 above the eyebrows of the attendant and about the ears of the attendant. In this position, a large portion of the hair of the attendant is covered. This avoids hair from falling into a clean or restricted area, or onto a patient.

When it becomes necessary to approach a patient that is bleeding or possibly having convulsions that may result in vomiting, the attendant should grip the forward portion of the cap 11 and pull the entire cap downward. The cap will then be in the position shown in FIGS. 1, 3 and 4. When he pulls it downward, the forward portion of elastic 17 will fit under the chin of the attendant. The rearward portion of elastic 17 will slide upward to the upper portion of the back of the user's head, as shown in FIG. 4. It will be near the top of the user's head, exposing the hair on the back of the attendant's head. In such emergency conditions, however, the risk of some hair of the attendant falling into the restricted area is not a serious problem. The strap 23 will stretch across the back of the user's head to provide additional retension.

In this shielding position, the attendant can perform the required medical treatment. If blood spurts toward the face of the attendant, the shield 19 will shield the face of attendant from contact with the blood. If blood contacts the cap 11 outside of the shield 19, the material of top 13 will normally shield the user's head from contact with the blood. Breathing is accommodated through the material of the top 13. Communication is not hampered because of the light weight and thinness of the cap 11.

The invention has significant advantages. The cap is light in weight and comfortable to wear. It can be worn virtually at all times by many persons performing emergency relief. Consequently, it will be present when needed, and does not have to be retrieved from the storage cabinet or the like. Also, it serves to prevent hair from falling into the restricted area during normal wear. When needed, it quickly converts to a shielding device by a simple pull downward on the forward edge. Even in the shielding position, it is comfortable to wear and does not hamper the treatment required.

While the invention has been shown in only one of its forms, it should be apparent to those skilled in the art that it is not so limited, but is susceptible to various changes without departing from the scope of the invention.

We claim:

1. A protective device for the head, comprising in combination:
    a flexible cap of breathable material having a top and an opening adapted to fit over a user's head;
    elastic means for causing the edge of the opening of the cap to grip the user's head to retain the cap on the user's head; and
    a transparent liquid impervious shield stationarily secured to the top of the cap across a hole formed in the top of the cap, the breathable material of the cap surrounding the entire periphery of the shield, the elastic means allowing the cap to be worn in a first position with the shield on top of the user's head and facing upward, and in a second position with the cap pulled downward from the first position with the shield positioned over the user's face and a forward portion of the opening located under the chin of the user.

2. The device according to claim 1 wherein the elastic means comprises a strip of elastic extending substantially completely around the edge of the opening.

3. A protective device for the head, comprising in combination:
    a flexible cap having a bag-like configuration with a top adapted to fit loosely over a user's head, the cap being formed of a spun fibrous breathable material;
    elastic means extending around the edge of the cap for causing the cap to grip the user's head to retain the cap on the user's head; and
    a transparent liquid impervious plastic shield stationarily secured across a hole formed in the top of the cap, the breathable material of the cap surrounding the entire periphery of the shield, the material of the shield being stiffer than the top of the cap, the elastic means allowing the cap to be worn in a first position with the shield on top of the user's head and facing upward, and in a second position with the cap pulled downward from the first position with the shield positioned over the user's face, the shield being of a size sufficient to allow the user to see through the shield when the cap is in the second position.

4. The device according to claim 3 further comprising:
    strap means secured to the cap for placement across the back of the user's head when in the second position to retain the cap on the user's head in the second position.

5. A method of protecting the face of a medical attendant from body fluids of a patient and for preventing hair of the attendant from falling from the user's head while in a restricted area, comprising in combination:
    providing a flexible cap for placement over the attendant's head;
    providing the cap with a liquid impervious transparent shield stationarily mounted so that the entire periphery of the shield is surrounded by the cap;
    providing the cap with elastic means for gripping the attendant's head;
    placing the cap in a first position on top of the attendant's head with the shield positioned over the attendant's head and facing upward, covering a substantial part of the attendant's hair to prevent hair from falling while in the restricted area; then
    to shield the attendant's face from contact with body fluids of a patient, pulling the cap downward from the first position to a second position with the shield over the face of the attendant, and with the elastic means retaining the cap in the second position.

6. The method according to claim 5, wherein in the second position, a forward portion of the elastic means fits snugly under the chin of the attendant.

7. The method according to claim 6, wherein in the second position, a rearward portion of the elastic means locates upward on the back of the attendant's head from the position that the rearward portion of the elastic means is normally located while in the first position.

* * * * *